(12) United States Patent
Spartz et al.

(10) Patent No.: US 11,143,589 B2
(45) Date of Patent: Oct. 12, 2021

(54) FTIR SPECTROMETER WITH CUT-OFF FILTER FOR HYDROGEN SULFIDE DETECTION

(71) Applicant: MLS ACQ, Inc., East Windsor, CT (US)

(72) Inventors: Martin L. Spartz, Ellington, CT (US); Anthony S. Bonanno, Ellington, CT (US); Kelly Renee McPartland, West Hartford, CT (US)

(73) Assignee: MLS ACQ, Inc., East Windsor, CT (US)

( * ) Notice: Subject to any disclaimer, the term of this patent is extended or adjusted under 35 U.S.C. 154(b) by 0 days.

(21) Appl. No.: 16/819,853

(22) Filed: Mar. 16, 2020

(65) Prior Publication Data
US 2020/0292447 A1   Sep. 17, 2020

Related U.S. Application Data

(60) Provisional application No. 62/818,988, filed on Mar. 15, 2019.

(51) Int. Cl.
*G01B 9/02* (2006.01)
*G01N 21/3518* (2014.01)
*G01N 33/00* (2006.01)
*G01N 21/35* (2014.01)

(52) U.S. Cl.
CPC ..... *G01N 21/3518* (2013.01); *G01N 33/0044* (2013.01); *G01N 2021/3595* (2013.01); *G01N 2201/1247* (2013.01)

(58) Field of Classification Search
CPC .......... G01N 21/3504; G01N 21/3518; G01N 33/0044; G01N 2021/3595; G01N 2201/1247
See application file for complete search history.

(56) References Cited

U.S. PATENT DOCUMENTS

| | | | |
|---|---|---|---|
| 6,853,452 B1* | 2/2005 | Laufer | G01N 21/3504 356/436 |
| 2015/0260695 A1* | 9/2015 | Spartz | G01N 30/8606 250/339.01 |
| 2016/0245742 A1* | 8/2016 | Case | G01N 33/22 |

* cited by examiner

*Primary Examiner* — Tarifur R Chowdhury
*Assistant Examiner* — Jonathon Cook
(74) *Attorney, Agent, or Firm* — HoustonHogle LLP

(57) ABSTRACT

A gas analysis system with an FTIR spectrometer preferably utilizes a long path gas cell, a narrow band detector, and an optical filter that narrows the detection region to measure hydrogen sulfide.

20 Claims, 11 Drawing Sheets

FTIR SPECTROMETER WITH CUT-OFF FILTER FOR HYDROGEN SULFIDE DETECTION

RELATED APPLICATIONS

This application claims the benefit under 35 USC 119(e) of U.S. Provisional Application No. 62/818,988, filed on Mar. 15, 2019, which is incorporated herein by reference in its entirety.

BACKGROUND OF THE INVENTION

Fourier transform infrared (FTIR) spectrometers with State-of-art Sigma Delta (digitizers) converters can in some cases provide the full digitization of the FTIR signal down to the base noise level. But if the system is electronic noise limited due to the detector chosen, there will be a lower signal to noise ratio (SNR) and the detector will probably act in a non-linear fashion.

In addition, FTIRs generally do not have the SNR necessary to obtain single digit parts per billion (ppb) detection limits in a direct measurement. Even if a very long path gas cell is utilized, a large volume of gas is required to turn over the gas cell volume and this slows the response of the instrument. It can also cause the system to fail quality assurance/quality control (QA/QC) requirements of the Environmental Protection Agency (EPA) methods.

Laser based system can provide this capability, but they may not be able to separate all the compounds present if they are scanning over a very narrow spectral range. Also, laser systems are sometimes limited by source noise instead of detector noise.

State-of-the-Art photoacoustic systems have been proposed to get very low-level detection as well, but they must be run in a batch type mode. The sample must be drawn into the cell and then measured, so that pressure oscillations are not observed by the detector. These systems can also suffer from compounds condensing on the microphone and most are not able to run at high temperatures associated with emissions gases.

FTIR spectrometers are normally "detector noise" limited when properly configured. This means that the detector noise is the largest noise source in the instrument. Ideally, the detector noise is greater than the electronics, IR source and other noises. When the detector is the limiting noise source, as the light intensity increases on the detector, the SNR increases linearly (if a linear detector). In the visible range, the detectors are in many cases "Shot Noise" limited. This means that as the light on the detector increases, the noise also increases with that added intensity, so there is less advantage to additional light intensity or multiplexing many wavelengths.

SUMMARY OF THE INVENTION

Unfortunately, many FTIR spectrometer gas analyzers utilizing HgCdTe (MCT) detectors are not detector noise limited but electronic noise limited, so increasing the light intensity after a point does not produce any enhancements to the SNR. This is due in part to their electronics and digitizers, the high throughput of the gas cell and optics, and the sensitivity of the detectors used. Having a detector with significantly higher sensitivity (like a narrow band 4 or 5 μm detector) will also see no improvement since its noise is 10 times lower than that of a standard detector.

InSb and InGaAs detectors are known to be more linear and could be utilized to get a more linear signal but if they are not the limiting noise source then the lowest SNR is not achievable.

A simple way to determine if an instrument is electronics noise limited is to turn up the detector preamp gain on a low signal to see if the SNR improves. If it does, the instrument is not detector noise limited. Increasing the preamp gain increases the detector noise and signal equally, so no enhancement should be noticed if the detector noise is the limiting noise.

One other problem with FTIR systems is that they can produce double modulation and if water is present the double modulation of the water shows up in the region where hydrogen sulfide ($H_2S$) and other environmentally important compounds are measured. This limits the ability of the FTIR to measure very low-level $H_2S$.

In general, according to one aspect, the invention features a Fourier transform infrared spectrometry system for measuring hydrogen sulfide, comprising a source for generating light, an interferometer for receiving the light, a sample cell containing a gas sample, a detector for detecting the light after passing through the sample gas, and a bandpass filter for filtering light prior to being detected the detector including 3,700 $cm^{-1}$ or 2,700 $cm^{-1}$.

In embodiments, the detector is an MCT detector with possibly at least an 8 μm cutoff or at least a 5 μm cutoff.

Typically, the optical filter has a bandpass of less than 300 cm-1 and preferably less than 100 cm-1.

Currently, an AutoRef operation is employed. Specially, a controller, detecting an output of the detector as the interferometer is scanned, processes interferograms within the bandpass of the bandpass filter at two resolutions and using the interferograms processed at a lower resolution as a background for interferograms processed at a higher resolution. Cosine apodization is also helpful, along with adding a filter spectrum of the filter into a regression analysis.

Finally, especially when detecting hydrogen sulfide in petroleum products including natural gas, the gas sample is preferably pressurized in the sample cell.

In general, according to another aspect, the invention features a spectrometry method, comprising analyzing a gas sample with a Fourier transform infrared spectrometer, detecting the light after passing through the sample gas with a detector, and filtering light prior to being detected to include 3,700 $cm^{-1}$ or 2,700 $cm^{-1}$ to measure hydrogen sulfide.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Now that we have had significant success in the reduction in overall system noise, lower detection limits are possible for compounds like $H_2S$. Traditionally, this has been a very difficult compound to measure by infrared spectroscopy due to its very weak infrared absorption. In addition, this technique would also work for other compounds that absorb IR light in the 1 to 5 µm spectral region.

The present system allows us to generate noise levels that allow for single digit part per billion (ppb) detection of gases with a direct reading FTIR. In the case of $H_2S$, it allows for detection to low ppm or high ppb.

Figure 1:
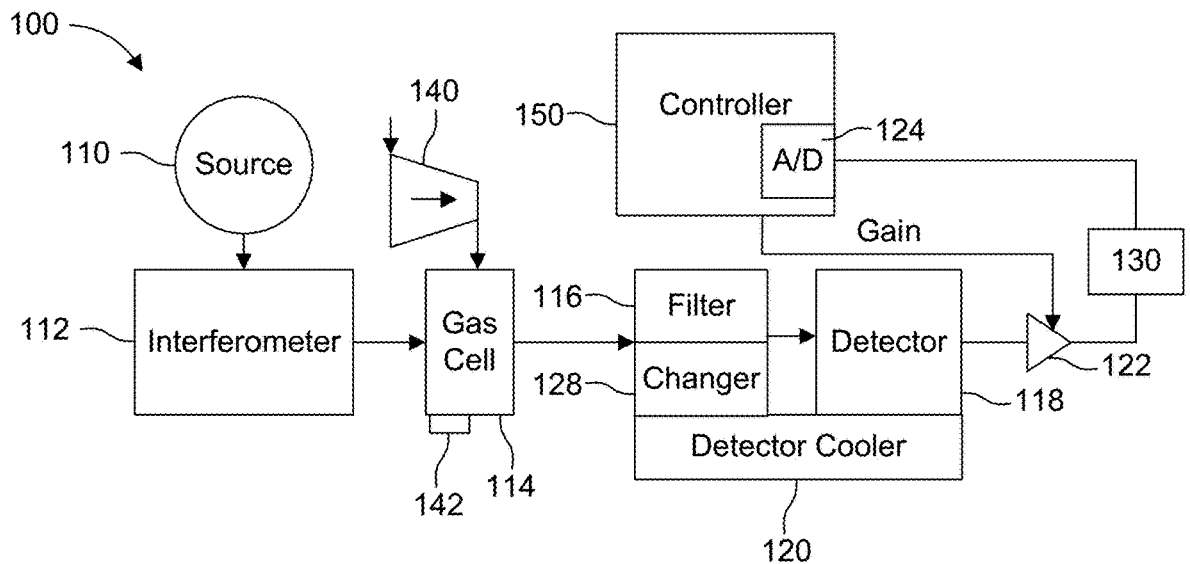
FIG. 1 is a block diagram of a Fourier transform interferometer (FTIR) spectrometer configured according to the principles of the present invention.

FIG. 1 shows an exemplary FTIR spectrometer 100.

Light is generated by a source 110. Common sources are heated silicon carbide elements, tungsten-halogen lamps and other thermal sources. Other infrared sources are Nernst Glower (operating at 2,000° C.) or a Plasma Source (Energetics-Hamamatsu) (operating at 10,000-12,000° C.).

The light is coupled into an interferometer 112, such as a Michelson interferometer including a mirror scanned under the control of a controller 150.

The light from the interferometer 112 passes through a gas cell 114 containing the sample. Currently, the cell 114 is a multiple pass gas cell, but a single pass gas cell could be used.

The light is then detected by a detector 118. To get the best SNR, a 4 or 5-µm cutoff MCT detector 118 with very high D* sensitivity is utilized. Specifically, the detector 118 only measures light having a wavelength of less than 8 µm, and preferably less than 5 µm. Due to this narrow detector bandpass only gases that absorb, i.e., have characteristic absorption features, in the 1 to 4 or 5 µm region can be measured.

Other possible detectors include a standard InSb detector that is TEC-cooled or 3 µm InAs detector that is TEC-cooled for natural gas applications.

An optical filter 116 with a passband of less than 450 cm$^{-1}$ bandpass filters the light received by the detector 118. Typically the passband is smaller such as less than 300 cm$^{-1}$, and its passband width is often between 100 and 200 cm$^{-1}$. Preferably, the filter 116 is placed in front of the detector 118. Typically, the center wavelength of the filter's passband is between 3 and 4 µm.

In more detail, the $H_2S$ filter is configured to pass the band of 3,600-3,800 cm$^{-1}$ for natural gas applications and the band 2,600-2,750 cm$^{-1}$ for ambient air, process or combustion applications.

It should be noted that the filter 116, can be placed anywhere and are generally positioned near a focal point but could be in a collimated beam as well. The filter 116 used one implementation has a 25 millimeter (mm) diameter or clear aperture and is a few millimeters thick.

Since most of the light is now blocked by the filter 116, the gain of a preamplifier 122 of the detector 118 can be increased to improve the SNR even further. This gain adjustment only helps if the system 100 is not already detector noise limited. If the system 100 is electronics noise limited, the gain should be increased until the detector noise is twice that of the electronics or more, to get the best SNR.

Then since hydrogen sulfide is a narrow absorber, the FTIR 100 is preferably operated in the AutoRef mode. In this mode, the FTIR controller 150 uses the collected spectra as a self-reference. Specifically, the spectra are collected at higher resolution (0.5, 1.0 or 2.0 cm$^{-1}$) and these interferograms (Igrams) are processed two ways. First, at the resolution the Igrams were collected, then secondly, the Igrams are processed at some reduced resolution 2, 4 or 8 times lower. By processing the Igram two ways, the controller 150 generates a background spectrum for each sample spectrum. The high-resolution single beam is then the sample spectrum and the lower resolution single beam is the background spectrum. The resultant absorbance spectrum is the difference between those two resolutions. This ensures that the baseline does not drift because each sample spectrum is its own background spectrum. On the other hand, sharp features like water show up as "second derivative" type features, where the absorbance spectrum goes down, up, down around any absorption line. This methodology is very good for high resolution features but poor for lower resolution features, since the two spectra are near identical. The real advantage for this application is that each stored and processed Igram is both the sample and the background, so there is no baseline drift. Very small signals like 0.00002 abs can be now measured routinely.

According to a preferred embodiment, the filter 116 is housed within the detector assembly 118. As a result, the detector and optical filter are temperature stabilized such as by a cooler 120 for the detector 118. This approach removes any passband shift due to thermal changes of the filter 116. Preferably, the cooler is a thermoelectric cooler (TEC) or liquid nitrogen (LN2) depending on application and is controlled by the controller 150 to stabilize the temperature of the detector 118 and the filter 116.

Narrow band MCT detectors are very sensitive but can be very non-linear in response, by limiting the light reaching the detector to spectral areas of interest, the detectors can be made significantly more linear in response. During initial testing of the prototype the signal went from about 2.5 V to ~13 V by limiting the bandpass reaching the detector. This by itself is more than a 5-fold improvement in SNR due to a more linear response.

By limiting the light on the detector using the optical filter, the total detector signal is much less, so a larger gain can be used to further improve the SNR and lower the MDLs. FTIRs with very sensitive detectors sometimes struggle with the ability to digitize all the SNR that could be generated by the system because the system is not detector-noise-limited. If, the configuration is electronics noise limited, improvements can be made so that the detector is the limiting source by turning up the gain on the detector. But the detector gain can only be increased if the amount or total signal of light is limited.

The system uses an optical bandpass or long pass filter to limit the light striking the detector and uses an FTIR to provide the resolution necessary to predict the compound in the presence of other compounds like water, $CO_2$ and hydrocarbons.

Then since $H_2S$ is a narrow absorber the FTIR can be operated in the AutoRef mode. In this mode, the spectra are collected at higher resolution (0.5, 1.0 or 2.0 $cm^{-1}$) and these Igrams are processed two ways. First, at the resolution the Igrams were collected, then second, at some reduced resolution 2,4 or 8 times lower. By processing the Igram two ways a background spectrum is created for each sample spectrum. This assures the user that the baseline does not drift at all because each sample spectrum is its own background spectrum. Also, because a filter is being used the signal intensity can drift a bit as the filter changes position (tilts) or changes temperature. If each spectrum has its own background these problems are completely removed.

The use of 2×8 $cm^{-1}$ spectral processing was determined as an ideal method for $H_2S$ detection. ("2×8 $cm^{-1}$ spectral processing" refers to AutoRef processing with a 2.0 $cm^{-1}$ resolution spectra using a 8 $cm^{-1}$ as the AutoRef background.)

More specifically, 0.5×2 $cm^{-1}$ spectral processing is used for natural gas applications, 2×8 $cm^{-1}$ for spectral processing is used for ambient air, combustion and possibly natural gas applications, and 4×16 $cm^{-1}$ spectral processing is used for other ambient air and combustion applications.

Lastly, an apodization function that goes to zero at the extent of the function is utilized to minimize spectral artifacts. Cosine is an apodization that goes to zero at the extent of applied interferogram. This type of apodization generally removes any additional oscillations caused by the discontinuity in the Igram and the fact that the Igram is being processed at high and low resolution.

In one embodiment, a pressure transducer 142 is added to monitor the pressure in the gas cell 114 and supply this information to the controller 150. Moreover, a pump 140 is added to pressurize the sample contained in the gas cell. This is helpful for ambient, process and combustion applications. Here, the gas cell 114 has an optical path length of 5 to 10 meters (m). In operation, the controller 150 controls the pump 140 to pressurize the sample in the gas cell to 1-5 atmospheres (atm) of pressure.

The pump 140 is also helpful for natural gas and petroleum applications. Here, the gas cell 114 has an optical path length of 0.1-1 m and the controller operates the pump to pressurize the sample in the cell 114 to 1-50 atm of pressure. In many cases, the pump 140 is part of the natural gas source. The natural gas is pressurized in the pipeline or storage. The system just uses the high pressure as it comes in. This is a distinct advantage over other instrumental systems. The source's pressure is used to improve the sensitivity.

Figure 2:
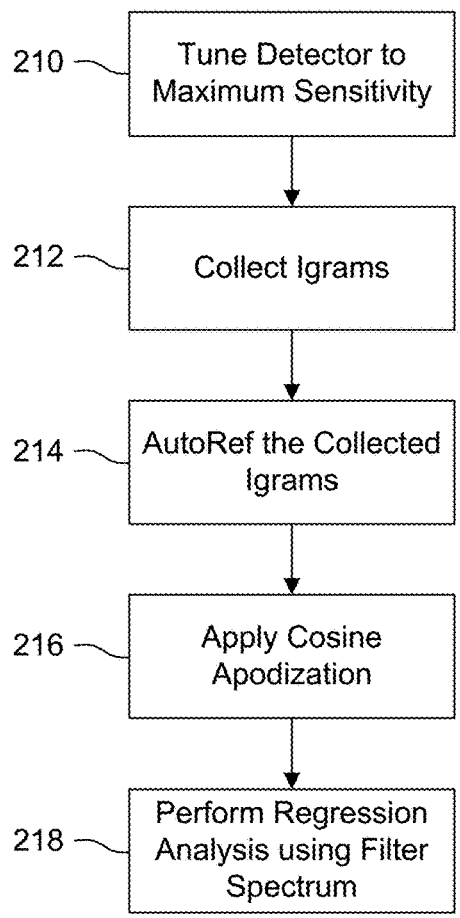
FIG. 2 is a flow diagram showing the operations performed by the spectrometer controller 150, according to the invention.

FIG. 2 is a flow diagram summarizing the processing and analysis performed by the controller 150.

In a first configuration step, the controller tunes the detector 118 for maximum sensitivity in step 210 by controlling the gain setting for the pre-amplifier 122.

Then the Igrams are collected in step 212 by the controller 150 scanning the interferometer 112.

The Igrams are then processed in the AutoRef mode in step 214.

Lastly, the apodization function is applied in step 218.

The spectral filter 116 can add its own spectral features to the spectrum. If the instrument is running with $N_2$ or a non-absorbing gas through the gas cell, a spectrum of the filter can be obtained, and that spectrum is added to the analysis software, so that these features are removed in the analysis. In this case, by doing so the residual spectra could be up to 10 times smaller than would otherwise be possible.

There are a number of advantages of this technology over prior methods and other optical technologies.

Much higher SNR allows for much lower detection limits for a limited number of compounds. But it provides a platform to offer numerous optical windows that can be optimized for certain compounds. The current system would be good for formaldehyde, acetaldehyde, acrolein and a few other compounds. In contrast, a laser with similar sensitivity would be good for only one compound.

One deployment strategy is to offer the analyzer as a 1-5 μm system. Then have filters (or filter wheel) and a second preamp that are placed into the system when a single gas is needed at very low levels. That way the user can use it as a broad-based analyzer or a narrow based analyzer and would not need to understand the electronics associated with getting these very low levels.

Figure 3:
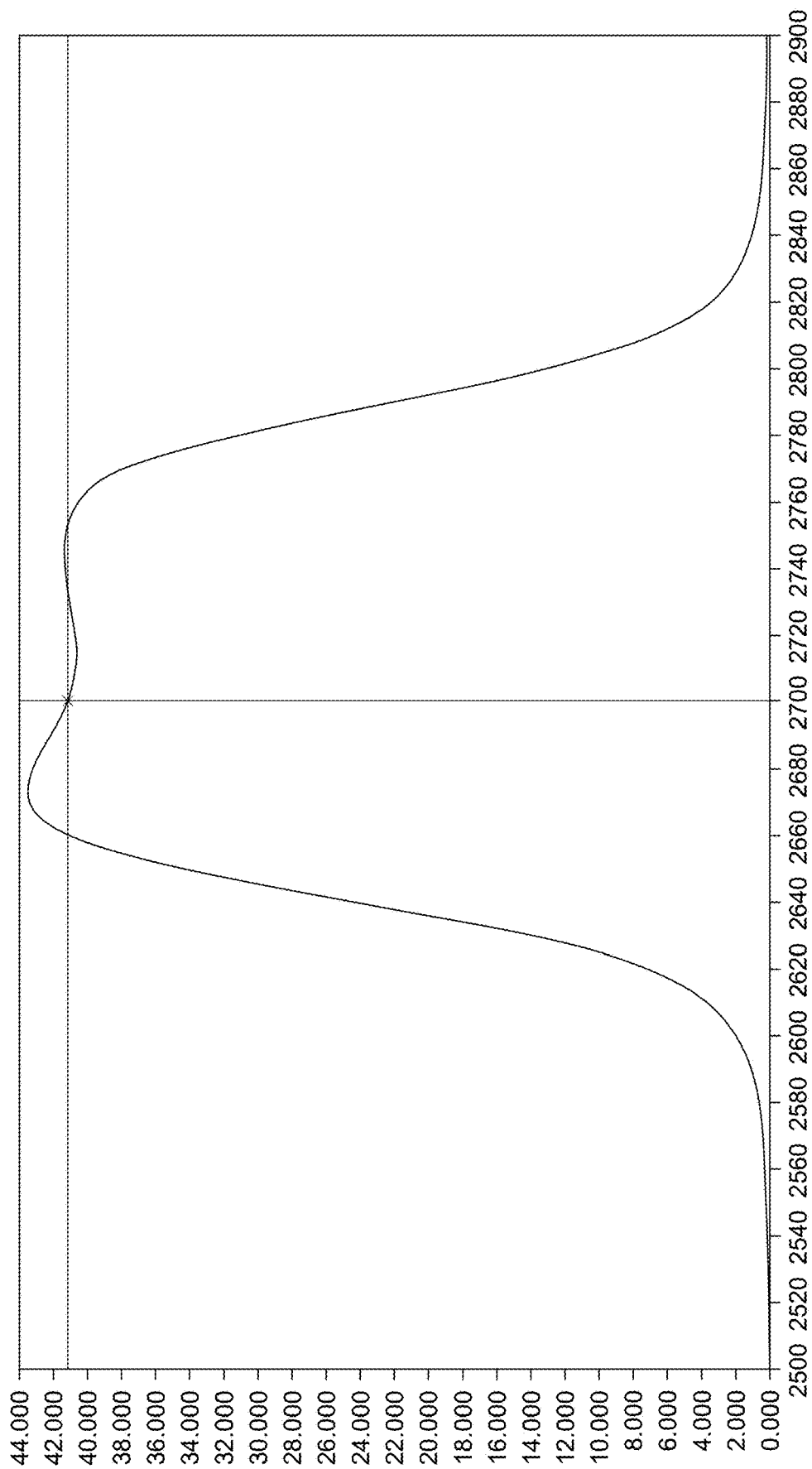
FIG. 3 shows an optical bandpass filter function for filter 116 for $H_2S$ determination in combustion and ambient air streams.

Detailed Analysis:

FIG. 3 shows an optical bandpass filter function for filter 116 for $H_2S$ determination in combustion and ambient air streams. The passband is centered around 2700 $cm^{-1}$.

As mentioned above, the detector signal is now linear, so no linearizer constants are required, and the optimum SNR is achieved. The single beam spectrum outside the filter band pass is nearly zero with no linearizer constants. With a signal of 40+ units, even a small non-linearity would have no effect on the quantification of the $H_2S$.

Since no artificial detector linearization is required, the system can be run AC-coupled, meaning there is no need to measure the DC component. This allows us to turn the detector gain all the way up and fill the digitizer range with the biggest signal possible. As the light intensity falls or is reduced from absorption, there is no DC signal that can drop and cause the signal to fall off the digitizer range.

Figure 4:
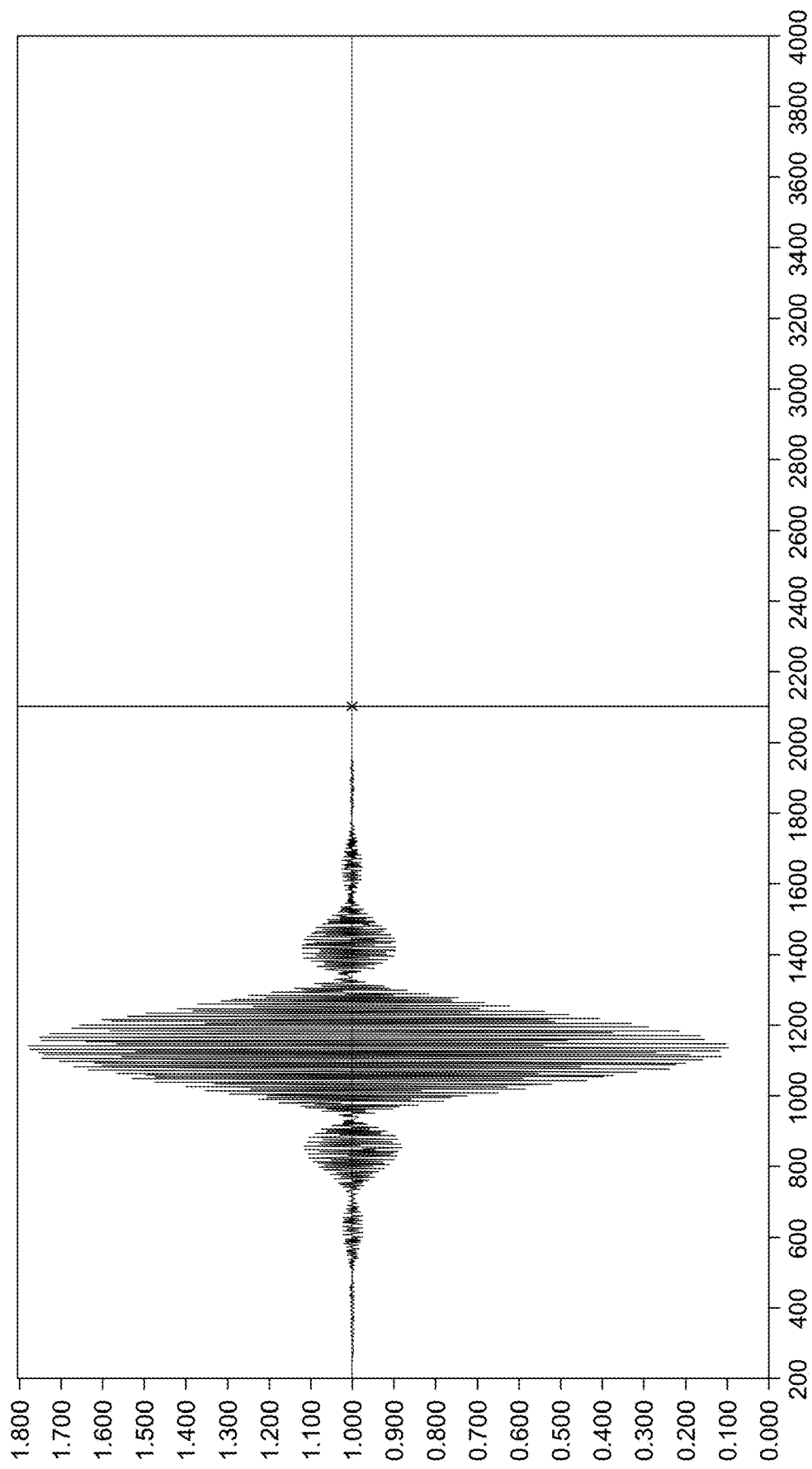
FIG. 4 shows the centerburst region of an interferogram from a $H_2S$ filter centered around 2,700 cm$^{-1}$.

FIG. 4 shows the centerburst region of an interferogram (points 800-1,600) from a $H_2S$ filter centered around 2,700 $cm^{-1}$.

With a narrow bandpass filter an interesting interferogram with lots of structure around the centerburst is generated.

Figure 5:
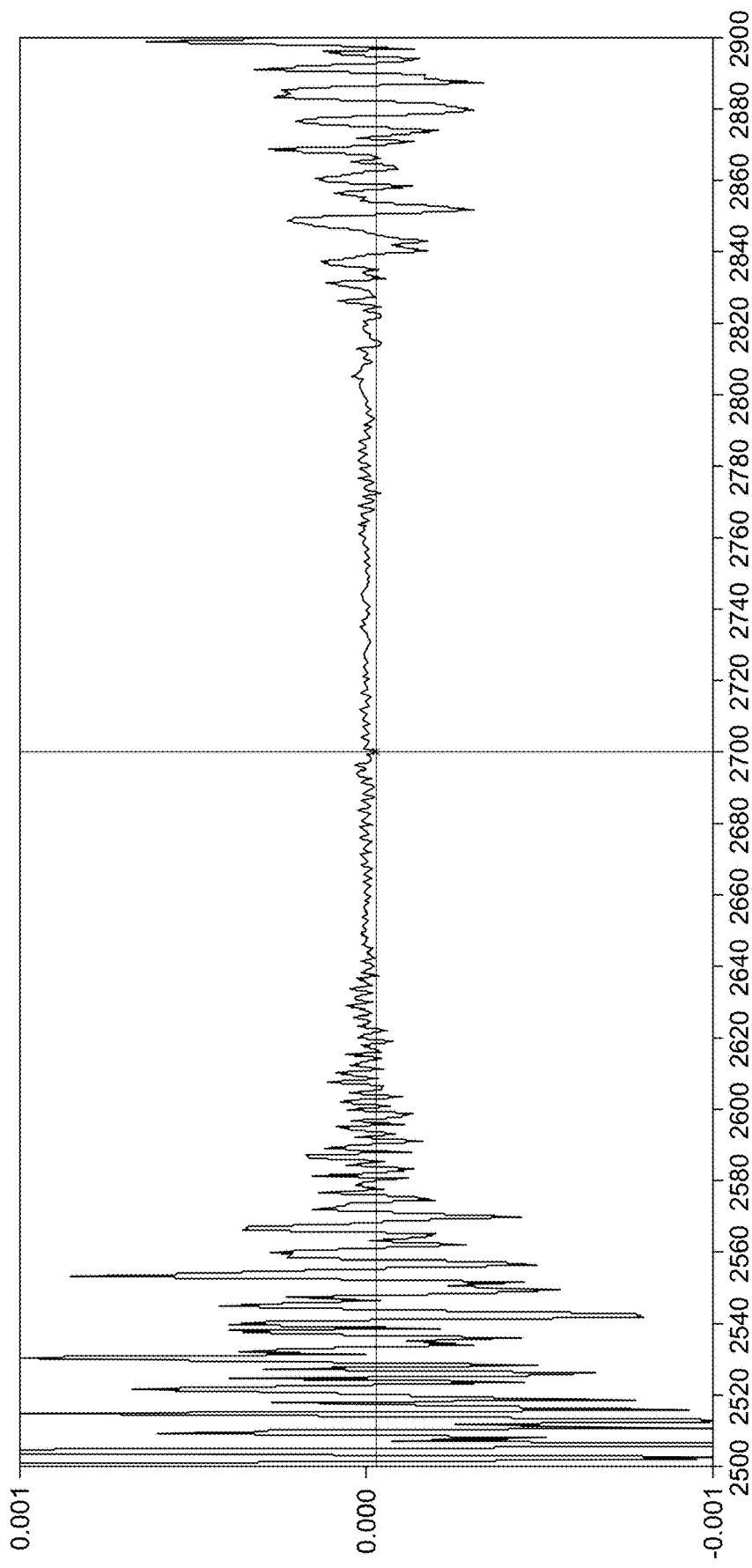
FIG. 5 shows a 2 cm$^{-1}$ by 8 cm$^{-1}$ AutoRef absorbance spectrum of the optimized $H_2S$ filter.

FIG. 5 shows a 2 $cm^{-1}$ by 8 $cm^{-1}$ AutoRef absorbance spectrum of the optimized $H_2S$ filter. Note some of the features on the right and left due to the AutoRef function. Also, note that the noise in the middle is equally centered around zero.

$H_2S$ Sensor for Ambient Air, Process and Natural Gas

The previous description outlines the use of an FTIR with a narrow band optical filter to produce the best MDLs possible over a narrow spectral range (100-200 $cm^{-1}$).

$H_2S$ is a very similar molecule to $H_2O$ and has a similar rovibrational spectrum but at slightly lower frequencies due to sulfur being heavier than oxygen. However, $H_2S$ has a significantly weaker spectrum because hydrogen and sulfur have nearly identical electronegativity which produces a very weak dipole moment.

Figure 6:
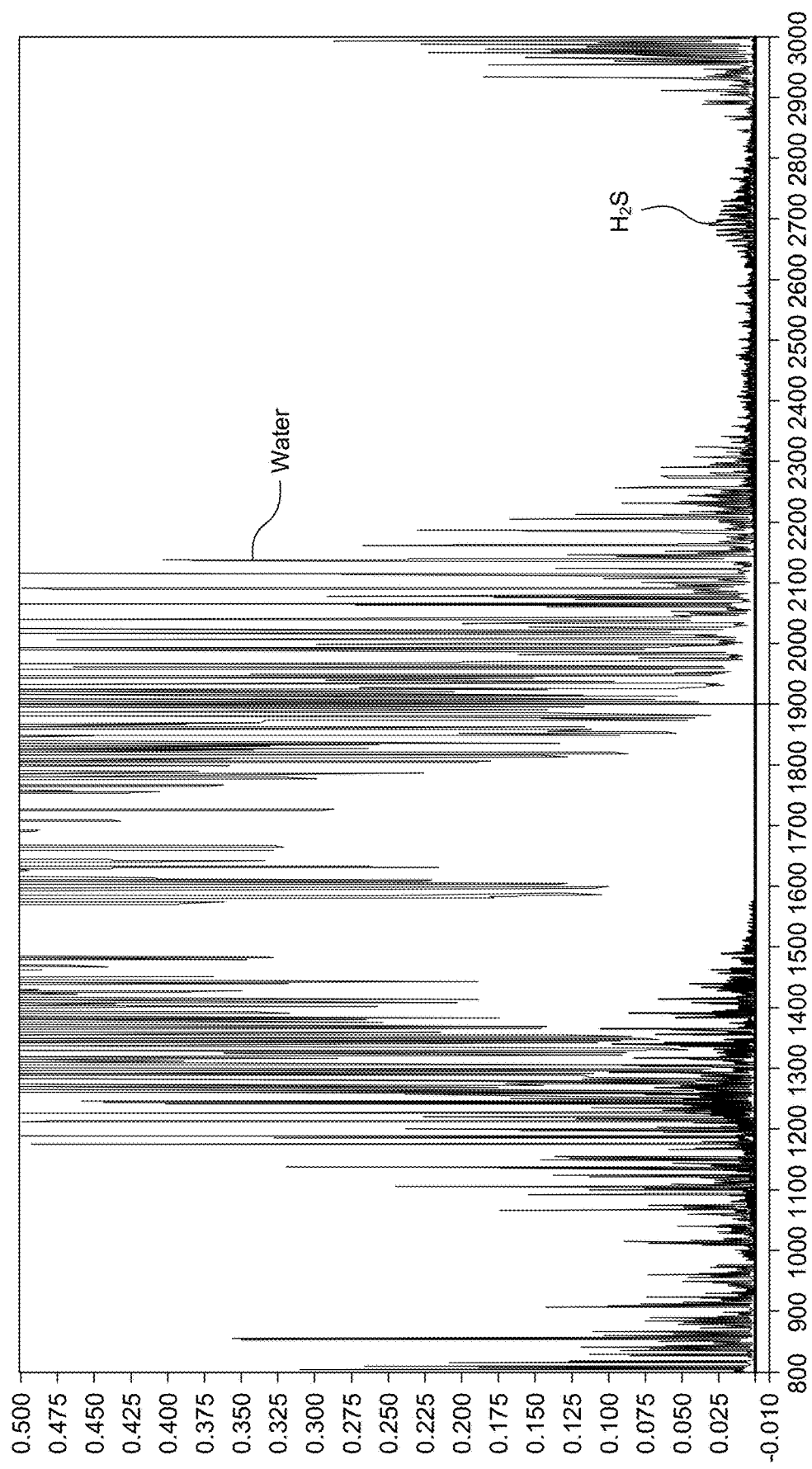
FIG. 6 is a spectral plot showing water and hydrogen sulfide.

As shown in the spectral plot of FIG. 6, the $H_2O$ is >100 times stronger absorber than the same concentration of $H_2S$. Due to this very weak spectrum, $H_2S$ is almost never measured by FTIR spectrometry.

Using standard FTIR gas analyzer technology, detection limits for $H_2S$ are normally limited to about 50-100 ppm in ambient air or emissions from combustion sources with strong interferences from $CH_4$ and $H_2O$. By utilizing the filtered-FTIR approach above, "AutoRef" technology, and analyzing the 2,700 $cm^{-1}$ region, a much lower MDL is achieved with little to no interference by $CH_4$ or $H_2O$.

Figure 7:
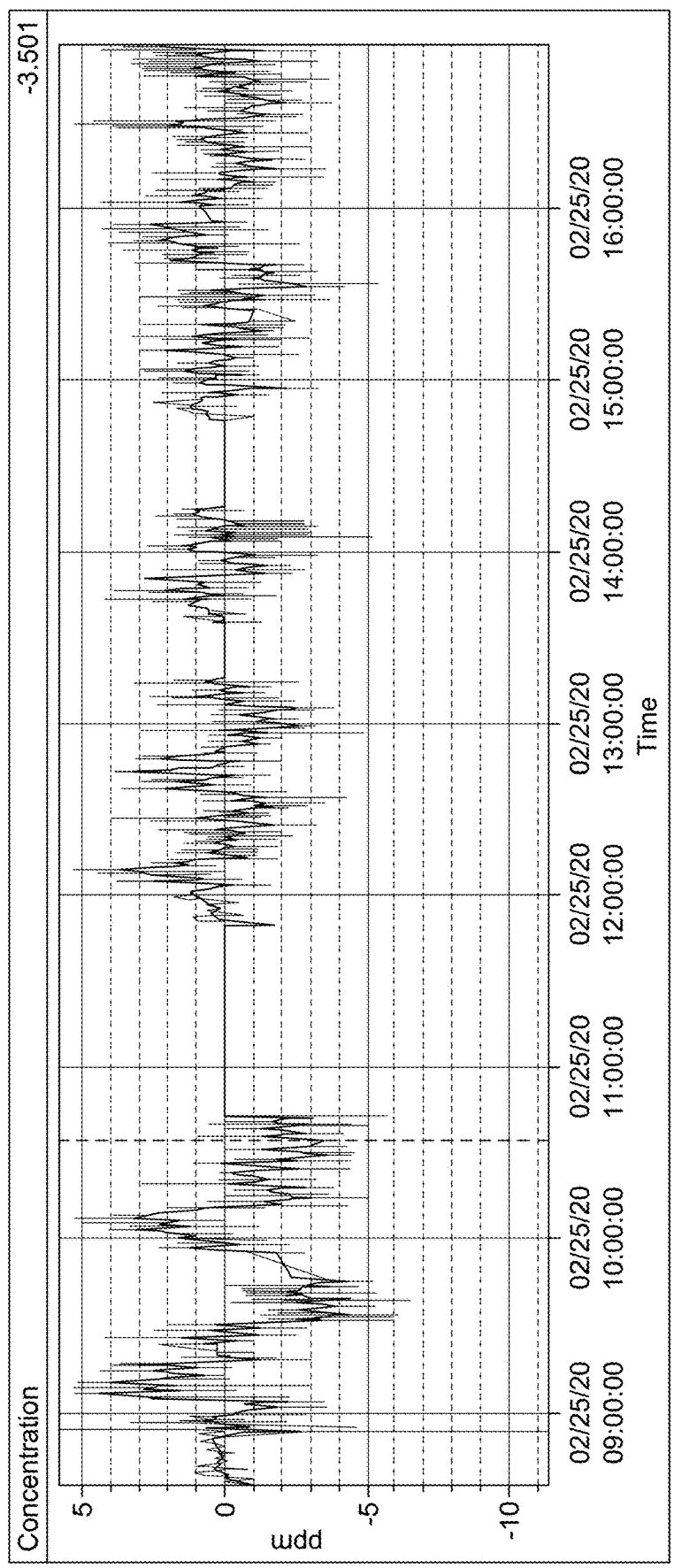
FIG. 7 shows standard deviation for $H_2S$ is about 2 ppm with an MDL of 6 ppm for a 15 second measurement using 2×8 cm$^{-1}$ resolution.

In FIG. 7, the standard deviation for $H_2S$ is about 2 ppm with an MDL of 6 ppm for a 15 second measurement using 2×8 $cm^{-1}$ resolution. These data were also collected with up to 40% moisture starting on the left and dropping to less than 1% on the right, demonstrating that water has minimal bias on the $H_2S$ measurement in this spectral region.

A 4 point rolling average would put the standard deviation at 1 ppm with an MDL of 3 ppm for a 1 minute average.

Figure 8:
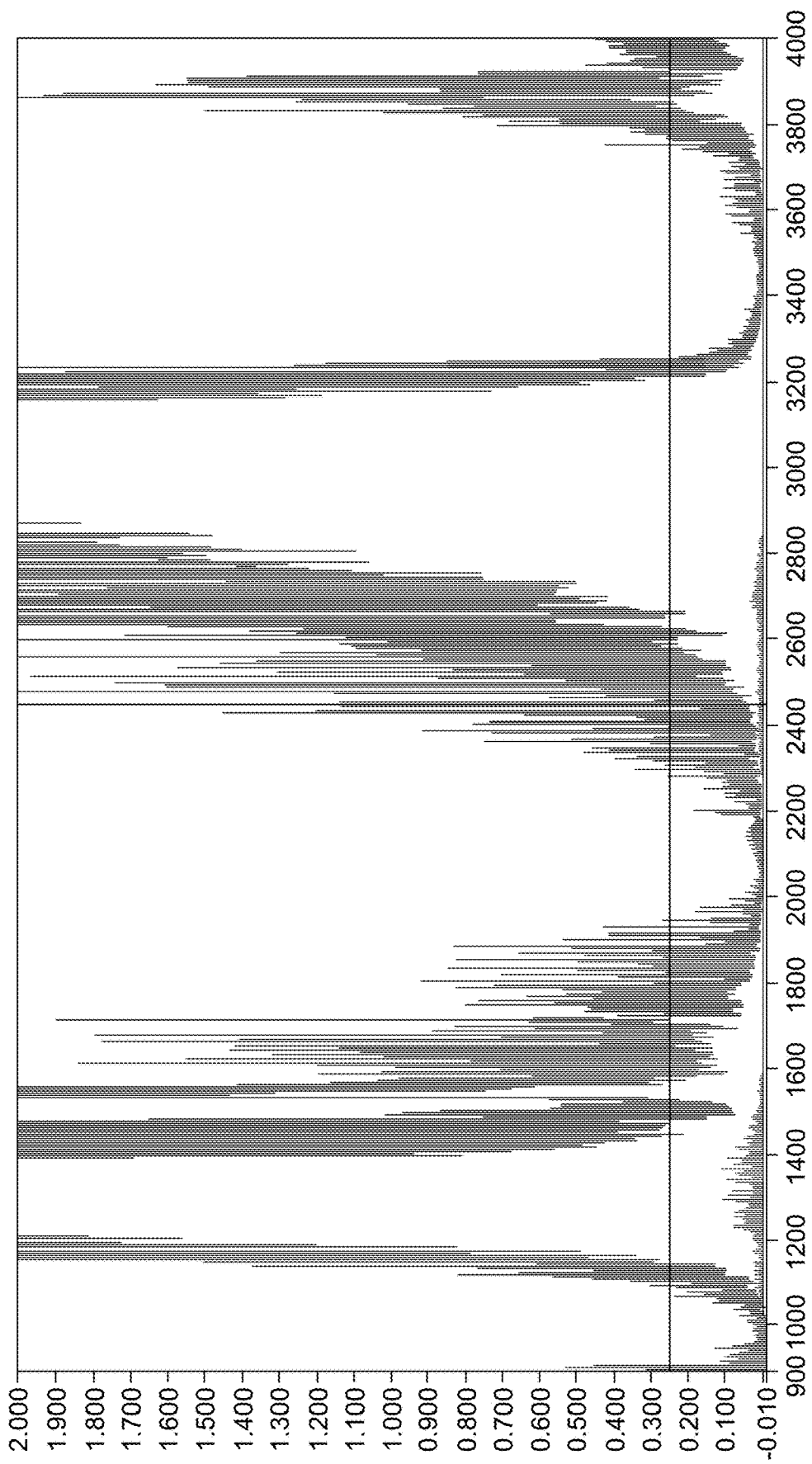
FIG. 8 shows a spectrum for very high levels of $CH_4$ (~100%)

FIG. 8 shows a spectrum for very high levels of $CH_4$ (~100%). The IR light in the 1,300 and 2,700 $cm^{-1}$ regions is completely absorbed, making measurement of $H_2S$ impossible. However, there is a third region around 3,650 $cm^{-1}$ ($H_2S$ combination band) where $CH_4$ has a much weaker IR absorption.

Figure 9:
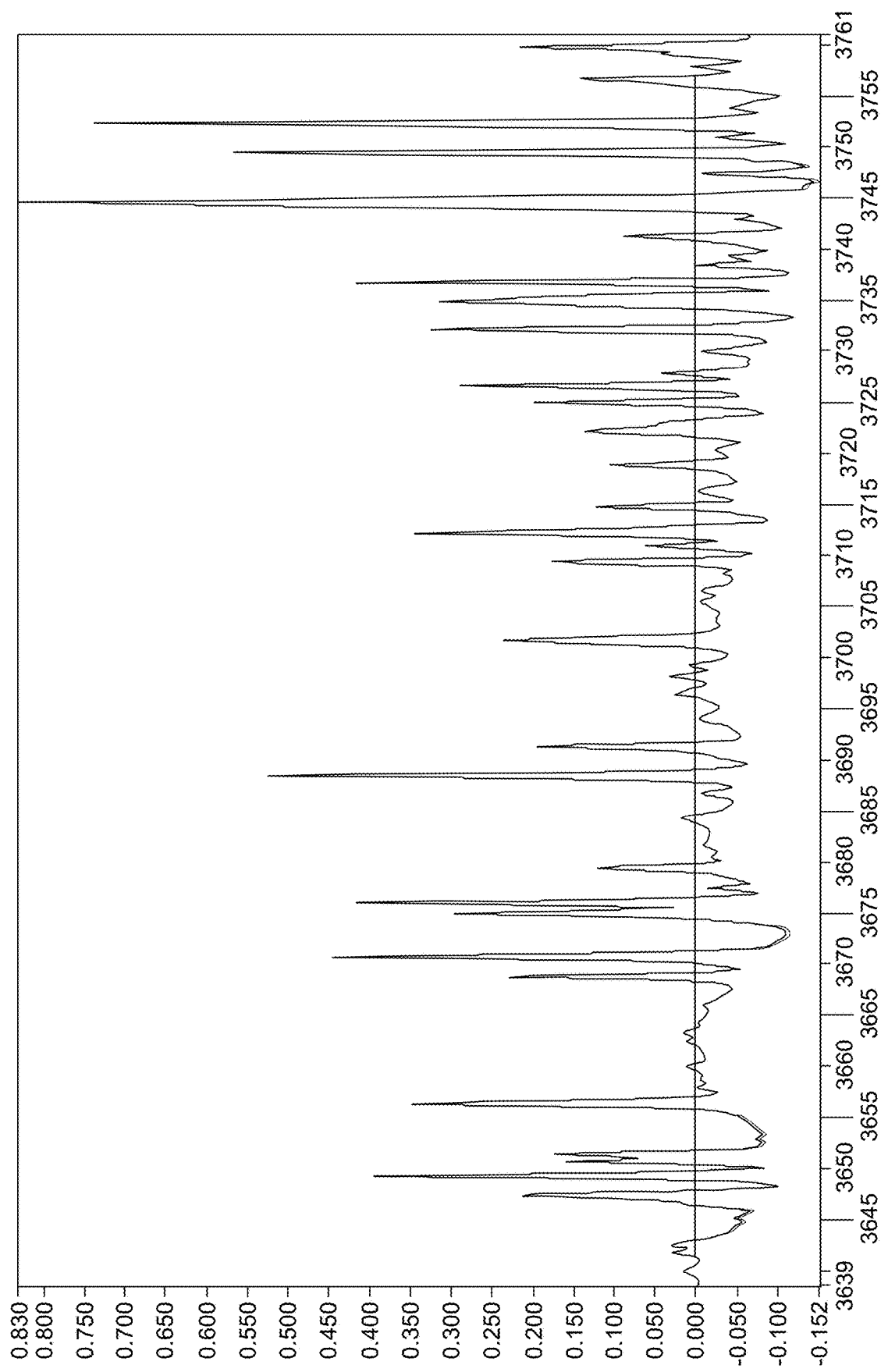
FIG. 9 shows the spectrum of a 90% $CH_4$ sample and an 80% $CH_4$ calibration spectrum.

For measurement of $H_2S$ in high levels of $CH_4$, we will again incorporate filtered-FTIR approach above and "AutoRef" (0.5×8 $cm^{-1}$), with the addition of the 3,650 $cm^{-1}$ region. In the spectrum of FIG. 9, the white spectrum is a 90% $CH_4$ sample, the gray spectrum is a 80% $CH_4$ calibration spectrum, and the center line spectrum is the $H_2S$ calibration spectrum. Since the $H_2S$ concentration is expected to be close to zero the center line spectrum appears as a straight line.

Figure 10:
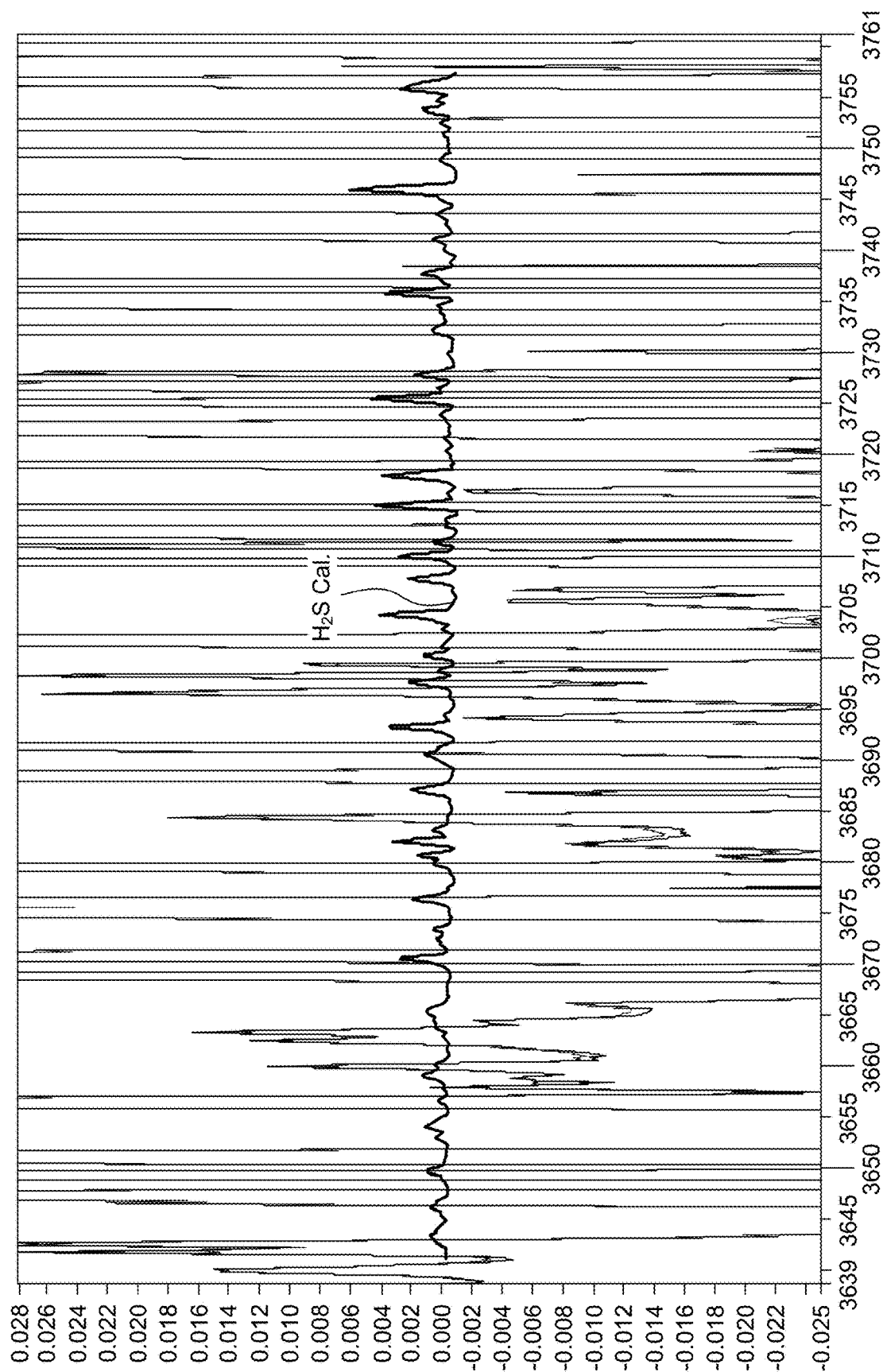
FIG. 10 shows a $H_2S$ calibration spectral features between the $CH_4$ lines.

If we expand the y-axis, we obtain the spectrum in FIG. 10. The $H_2S$ calibration spectral features can be observed between the $CH_4$ lines. This suggests that higher resolution FTIR data may be more appropriate for this analysis. By using multiple frequencies to monitor for $H_2S$ we reduce the potential bias in this measurement while increasing its precision.

Figure 11:
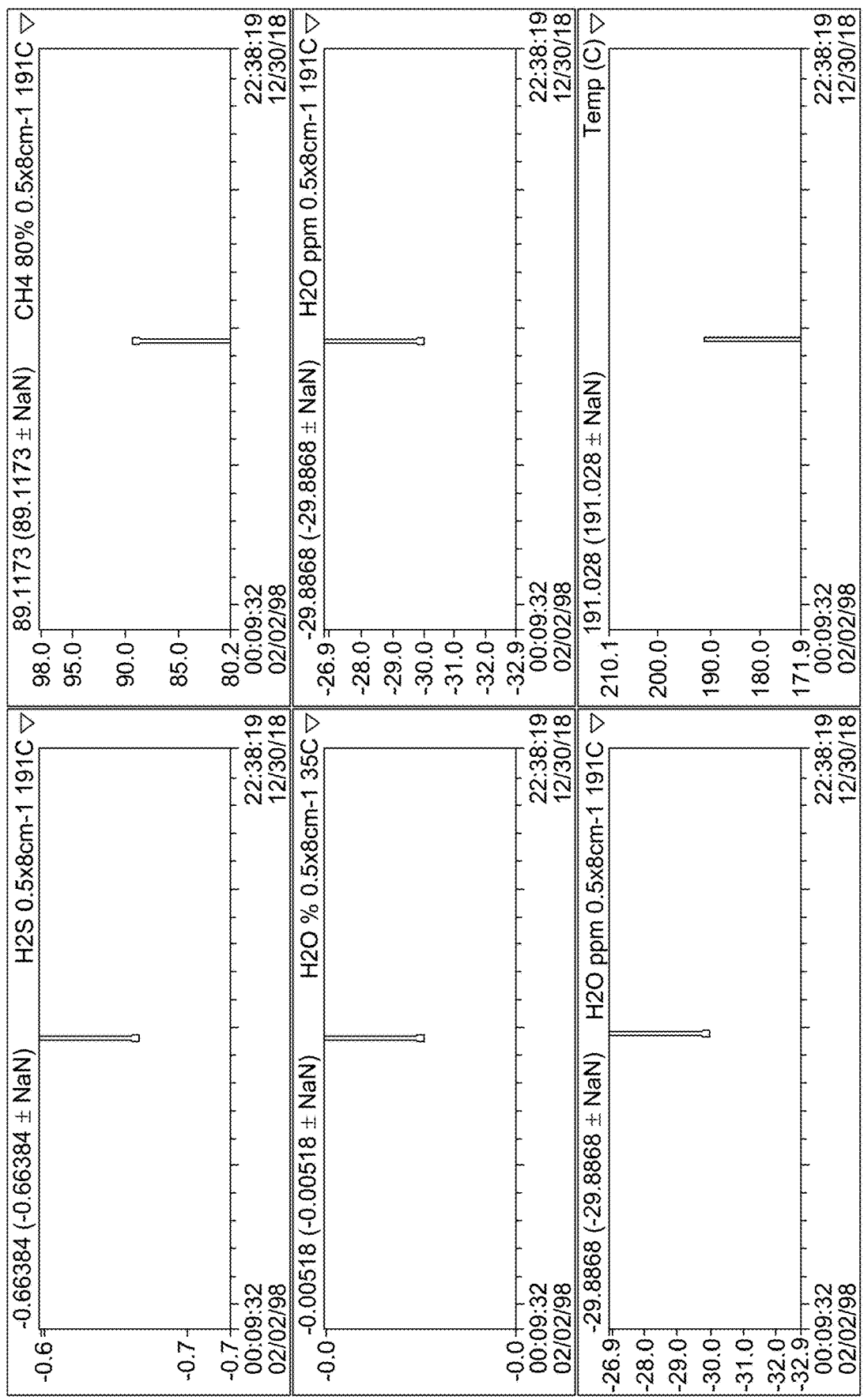
FIG. 11 shows the measured $H_2S$ result for the above methane spectrum is less than +/−1 ppm.

FIG. 11 shows the measured $H_2S$ result for the above methane spectrum is less than +/−1 ppm, which should be good enough for $H_2S$ determination in raw natural gas streams.

Figure 12:
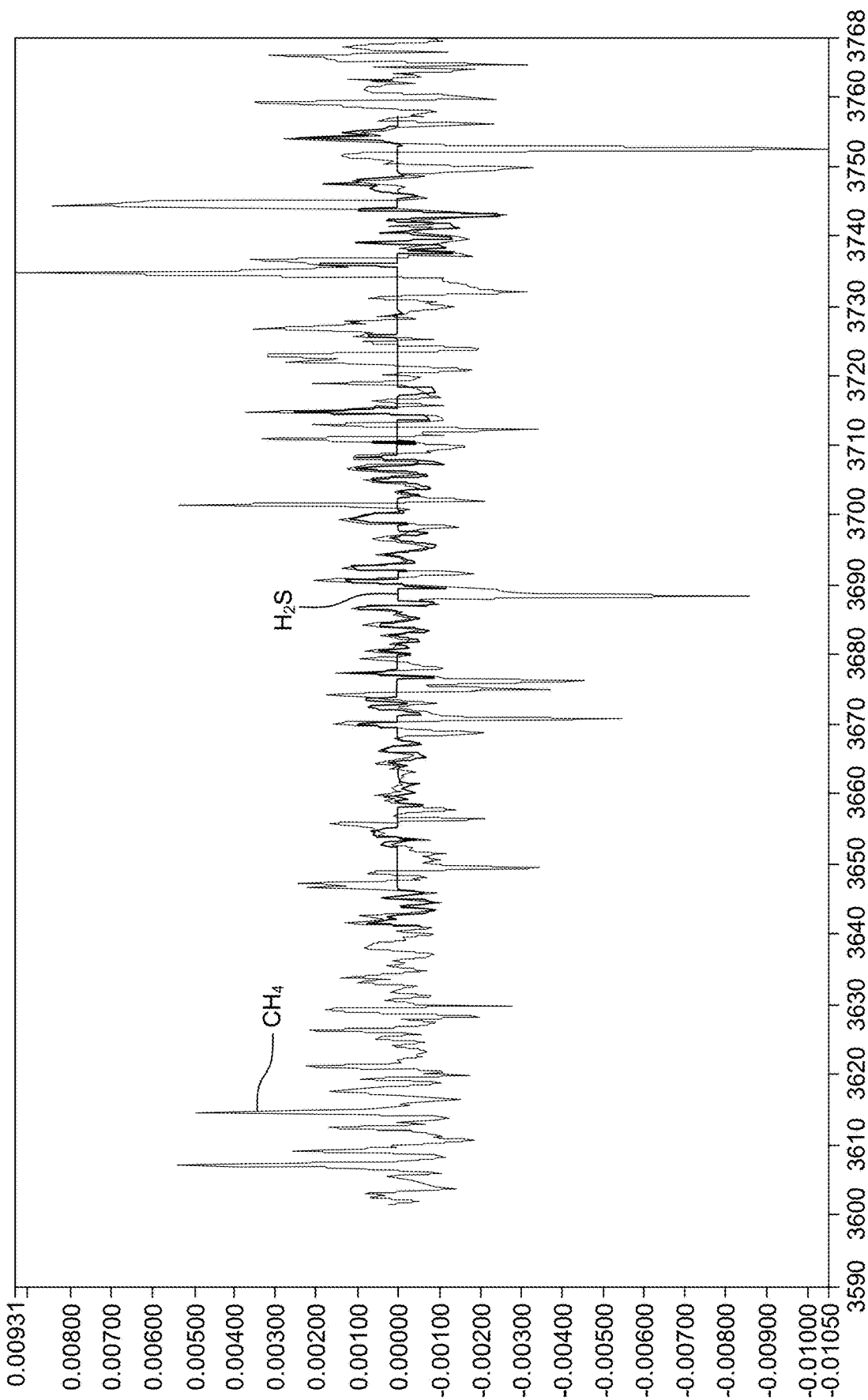
FIG. 12 shows the spectral residuals below for $H_2S$ and $CH_4$.

FIG. 12 shows the spectral residuals below for $H_2S$ and $CH_4$ show that by using high resolution we can select the best $H_2S$ bands to measure and generate the lowest possible residual spectrum and best result.

Laser based systems that measure compounds like $H_2S$ work better at lower pressures so that the absorption band of the compound is as narrow as possible. This limits the sensitivity of these systems. These systems only measure one absorption feature of the compound and as such can be affected by interfering species if not properly accounted for.

FTIRs by themselves are generally not utilized for compounds like $H_2S$ because the detection limits are on the order of 50-100 ppm and have very significant interferences with $CH_4$ and $H_2O$.

While this invention has been particularly shown and described with references to preferred embodiments thereof, it will be understood by those skilled in the art that various changes in form and details may be made therein without departing from the scope of the invention encompassed by the appended claims.

What is claimed is:

1. A Fourier transform infrared spectrometry system for measuring hydrogen sulfide, comprising:
    a source for generating light;
    an interferometer for receiving the light;
    a sample cell containing a gas sample;
    a detector for detecting the light from the interferometer and after passing through the sample gas;
    a bandpass filter for filtering light prior to being detected the detector including 3,700 $cm^{-1}$ or 2,700 $cm^{-1}$; and
    a controller for detecting an output of the detector as the interferometer is scanned and processes interferograms to measure a concentration of the hydrogen sulfide in the sample cell.

2. The system of claim 1, wherein the detector is an MCT detector.

3. The system of claim 1, wherein the detector has at least an 8 μm cutoff.

4. The system of claim 1, wherein the detector has at least a 5 μm cutoff.

5. The system of claim 1, wherein the optical filter has a bandpass of less than 300 $cm^{-1}$.

6. The system of claim 1, wherein the optical filter has a bandpass of less than 100 $cm^{-1}$.

7. The system of claim 1, wherein the controller processes the interferograms within the bandpass of the bandpass filter at two resolutions and using the interferograms processed at a lower resolution as a background for interferograms processed at a higher resolution.

8. The system of claim 7, wherein the controller employs cosine apodization.

9. The system of claim 7, wherein the controller adds a filter spectrum of the filter into a regression analysis.

10. The system of claim 1, further comprising the controller operating a pump pressurizing the gas sample in the sample cell.

11. A spectrometry method, comprising:
analyzing a gas sample with a Fourier transform infrared spectrometer;
detecting the light after passing through the sample gas with a detector; and
filtering light prior to being detected to include 3,700 cm$^{-1}$ or 2,700 cm$^{-1}$ to measure hydrogen sulfide; and
detecting an output of the detector as an interferometer of the Fourier transform infrared spectrometer is scanned and processing interferograms to measure a concentration of the hydrogen sulfide in the gas sample.

12. The method of claim 11, wherein the detector is an MCT detector.

13. The method of claim 11, wherein the detector has at least an 8 μm cutoff.

14. The method of claim 11, wherein the detector has at least a 5 μm cutoff.

15. The method of claim 11, further comprising filtering the light with a bandpass of less than 300 cm$^{-1}$.

16. The method of claim 11, further comprising filtering the light with a bandpass of less than 100 cm$^{-1}$.

17. The method of claim 11, further comprising processing the interferograms at two resolutions and using the interferograms processed at a lower resolution as a background for interferograms processed at a higher resolution.

18. The method of claim 17, further comprising employing cosine apodization to filter the interferograms.

19. The method of claim 17, further comprising adding a filter spectrum of the filter into a regression analysis.

20. The method of claim 11, further comprising pressurizing the gas sample in the sample cell.

* * * * *